US00PP28504P3

(12) United States Plant Patent
Bradford et al.

(10) Patent No.: US PP28,504 P3
(45) Date of Patent: Oct. 10, 2017

(54) PLUM TREE NAMED 'PLUMSWEET XVII'

(50) Latin Name: *Prunus salicina*
Varietal Denomination: Plumsweet XVII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 26 days.

(21) Appl. No.: 14/757,253

(22) Filed: Dec. 11, 2015

(65) Prior Publication Data

US 2017/0172025 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP18,687 P2 4/2008 Bradford
PP19,537 P2 12/2008 Bradford

*Primary Examiner* — Keith Robinson

(57) ABSTRACT

The present invention relates to a plum tree, *Prunus salicina*, and more particularly to a new and distinct variety broadly characterized by a large size, vigorous, hardy, and productive tree. Being self-unfruitful, the present variety requires cross pollination from an apricot, interspecific, or plum that blooms during the early season, such as 'Yummygem' plum tree (U.S. Plant Pat. No. 15,809). The present variety produces a heavy bloom with a moderate amount of pollen to entice good bee activity to facilitate pollination. The fruit matures under the ecological conditions described during late May, with first picking on May 25, 2015. The fruit is uniformly medium in size, a green and red two-tone in skin color, full red in flesh color, clingstone in type, oblate in shape, firm in texture, juicy, very sweet, and excellent in flavor.

1 Drawing Sheet

Botanical classification: *Prunus salicina.*
Varietal denomination: 'PLUMSWEET XVII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumsweet XVII'.

During a typical blooming season we isolate as seed parents both individual and groups of different plum and interspecific hybrid trees by covering them with screen houses. A hive of bees is placed inside each such house, and bouquets to provide pollen from different plum, apricot, and interspecific hybrid trees are placed in buckets near the trees approximately every two days for the duration of the bloom. During 2008, one such house containing 'Plumsweet VI' (U.S. Plant Pat. No. 18,687) interspecific tree was crossed by us in this manner. To pollinate this interspecific, we selected bouquets from several sources of plum trees without keeping specific written details. Upon reaching maturity the fruit from this interspecific tree was harvested, and the seeds were removed, cracked, stratified and germinated as a group with the label "H22". They were grown as seedlings on their own root in our greenhouse and upon reaching dormancy transplanted to a cultivated area of our experimental orchard located near Le Grand, Calif. in Merced County (San Joaquin Valley). During the spring of 2012 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to its seed parent, 'Plumsweet VI' interspecific tree (U.S. Plant Pat. No. 18,687), by being self-unfruitful and by producing fruit that is a green and red two-tone in skin color, full red in flesh color, firm in texture, juicy, and sweet in flavor, but is distinguished therefrom by being easier to set, by producing fruit that is larger in size and that matures about five days earlier.

The present variety is also similar to 'Blackred I' interspecific tree (U.S. Plant Pat. No. 19,537), by being self-unfruitful, by blooming in the early season, and by producing fruit that is full red in flesh color, firm in texture, juicy, clingstone in type, and oblate in shape, but is distinguished therefrom by producing fruit that is larger in size, that is somewhat sweeter in flavor, that is a green and red two-tone instead of blackish red in skin color, and that matures about five days later.

SUMMARY OF VARIETY

The present plum variety is characterized by a large size, vigorous, hardy, and productive tree. Being self-unfruitful, the present variety requires cross pollination from an apricot, interspecific, or plum that blooms during the early season, such as 'Yummygem' plum tree (U.S. Plant Pat. No. 15,809). The present variety produces a heavy bloom with a moderate amount of pollen to entice good bee activity to facilitate pollination. The fruit matures under the ecological conditions described during late May, with first picking on May 25, 2015. The fruit is uniformly medium in size, a green and red two-tone in skin color, full red in flesh color, clingstone in type, oblate in shape, firm in texture, juicy, very sweet, and excellent in flavor.

DRAWING

The accompanying photograph consists of four whole fruits positioned to display the characteristics of the skin color and form, one divided fruit to reveal the flesh and stone, a tip shoot growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of full ripe on Jun. 5, 2015, on the original tree during its seventh growing season. The flower and bud descriptions were developed during the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'Plumsweet VI' interspecific tree (U.S. Plant Pat. No. 18,687).

Pollen parent: Unknown plum.

TREE

Size: Large, reaching and maintaining a height of 15' [4.57 m.] and a spread of 7' [2.13 m.] after seven growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a Perpendicular V type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable early seasonal blooming apricot, interspecific, or plum, such as 'Yummygem' plum tree (U.S. Plant Pat. No. 15,809).

Bearing: Regular bearer, weather dependent, no crop failures observed as of yet.

Trunk:

*Size.*—Medium, reaching a maximum diameter of 4½" [114 mm.] after the seventh growing season.

*Texture.*—Medium.

*Bark color.*—A Moderate brown [58. m.Br] and Dark grayish brown [62. d.gy.Br] variegation with Dark brown [59. d.Br] crevices present.

*Lenticels.*—Approximate Number Per Square Inch: 5. Color: Brownish orange [54. brO]. Average Size: 5/16" [7.9 mm.] in length. The width is typically one fourth as much as the length. Shape: Eye-shaped.

Branches:

*Size.*—Medium, scaffold diameter is 2½" [64 mm] measured 12" above the crotch, diameter of first side hanger is ⅞" [22 mm.] measured 6" from the main scaffold.

*Texture.*—Fairly smooth on first and second year wood, increasing roughness with age.

*Color.*—1st Year Wood Topside: Grayish red [19. gy.R]. 1st Year Wood Underside: Strong yellow green [117. s.YG]. Older Wood: A Strong brown [55. s.Br] and Light grayish brown [60. l.gy.Br] variegation.

*Lenticels.*—Number Per Square Inch: About 25 on second year wood. Color: Light yellowish brown [76. l.yBr]. Average Size: Small, 1/64" [0.4 mm.] in length. The width is typically one fourth as much as the length. Shape: Eye-shaped.

Leaves:

*Size.*—Medium. Average Length: 4" [101.6 mm.]. Average Width: 2⅛" [54.0 mm.].

*Arrangement.*—Alternate.

*Thickness.*—Medium.

*Form.*—Elliptical.

*Apex.*—Acuminate.

*Base.*—Acute with an average angle base angle of 80 degrees.

*Surface.*—Smooth on both sides.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Topside is Moderate yellow green [120. m.YG] and the underside is Brilliant yellow green [116. brill.YG].

*Stipules.*—Number: 2 per leaf, up to 6 per growing tip. Average Length: ¼" [6.4 mm.]. Color: Moderate yellow green [120. m.YG] becoming Light grayish reddish brown [45. l.gy.rBr] with age.

*Glands.*—Number: Mostly 2 per leaf. Position: A slightly alternate, positioned at the intersection of the petiole and base of leaf blade. Form: Globose. Size: Small, 1/64" [0.4 mm.] in diameter. Color: Strong yellow green [117. s.YG] becoming Moderate reddish brown [43. m.rBr] in the center with age. Leaf buds: Pointed.

Flower buds:
*Hardiness.*—Hardy, with respect to central California blooming season.
*Diameter.*—Typically 3/16" [4.8 mm.] 1 week before bloom.
*Length.*—Typically 3/8" [9.5 mm.] 1 week before bloom.
*Form.*—Not appressed.
*Surface.*—Slightly pubescent.
*Tip color.*—White [263. White].

Flowers: Perfect, complete, perigynous, usually a single pistil, about thirty stamens, five sepals and petal locations alternately positioned.
*Average flower diameter.*—1 1/16" [27.0 mm.].
*Average flower depth.*—3/8" [9.5 mm.] when fully open.
*Average pedicel length.*—1/4" [6.4 mm.].
*Number of petals.*—Five, no double blossoms observed.
*Petal shape.*—Oval to circular.
*Petal margin.*—Entire, smooth to slightly wavy.
*Average petal diameter.*—9/16" [14.3 mm.].
*Average petal length.*—9/16" [14.3 mm.].
*Petal apex.*—Rounded.
*Petal base.*—Obtuse.
*Petal color.*—White [263. White] on both sides.
*Anther color.*—Brilliant yellow [83. brill.Y].
*Pollen production.*—Moderate, enticing to bees.
*Pollen color.*—Strong yellow [84. s.Y].
*Stigma color.*—Pale yellow green [121. p.YG].
*Stigma position.*—Located somewhat below the average anther position.
*Sepal color.*—Brilliant yellow green [116. brill.YG] on both sides.
*Sepal length.*—3/16" [4.8 mm.].
*Sepal width.*—5/32" [4.0 mm.].
*Sepal apex.*—Rounded to elliptical to match the width and length.
*Sepal margin.*—Fairly smooth with slight serrations toward the apex.
*Average pistil length.*—5/8" [15.9 mm.].
*Average stamen length.*—9/16" [14.3 mm.].
*Ovary.*—Smooth.
*Fragrance.*—Moderate.
*Bloom density.*—Heavy.
*Number per cluster.*—2 to 8, average 4.
*Blooming period.*—Early compared to other varieties, two days before 'Yummygem' plum (U.S. Plant Pat. No. 15,809).
*Onset of bloom.*—One percent on Feb. 12, 2015.
*Date of full bloom.*—Feb. 24, 2015.
*Duration of bloom.*—One to two weeks, dependent on ambient temperature.

FRUIT

Maturity when described: Full ripe, Jun. 5, 2015.
Date of first picking: May 25, 2015.
Date of last picking: Jun. 7, 2015.
Size: Uniform, medium.
*Average diameter axially.*—2 3/16" [55.6 mm.].
*Average diameter across cheek plane.*—2 11/16" [68.3 mm.].
*Average diameter across suture plane.*—2 5/8" [66.7 mm.].
*Typical weight.*—5.4 ounces [153 grams].
Form: Uniform, oblate, symmetrical.
*Longitudinal section form.*—Oblate.
*Transverse section through diameter.*—Round.
Suture: A shallow groove extending from the base to the apex.
Ventral surface: Rounded, slightly lipped toward the base.
Lips: Fairly equal.
Cavity: Flaring, slightly elongated on the suture plane.
*Depth.*—7/16" [11.1 mm.].
*Breadth.*—1" [25.4 mm.].
Base: Truncate, slightly cordate if viewed parallel to the suture.
Apex: Rounded to truncate.
Pistil point: An inconspicuous Deep reddish brown [41. deep rBr] dot located at the end of the suture.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Moderate.
*Tendency to crack.*—None observed.
*Color.*—A very deep red [14. v.deep R] with Light greenish yellow [101. l.gY] streaking and dappling with strong Moderate yellow green [120. m.YG] freckling stronger toward the apex.
*Lenticels.*—Number Per Square Inch: About 150 toward the apex. Average diameter: 1/48" [0.5 mm].
*Bloom.*—Moderate.
Flesh:
*Color.*—Very deep red [14. v.deep R] close to the skin smoothly blending to Strong red [12. s.R] toward the stone.
*Surface of pit cavity.*—Covered with Moderate red [15. m.R] broken fibers when twisted from stone.
*Amygdalin.*—Moderate.
*Juice.*—Abundant, rich.
*Texture.*—Firm, crisp.
*Fibers.*—Abundant, fine.
*Ripens.*—Fairly even.
*Flavor.*—A tasty blend of acid and sugar, typically 20 brix.
*Aroma.*—Slight.
*Eating quality.*—Excellent.

STONE

Type: Clingstone.
Form: Oval.
Hilum: Narrow.
Base: Rounded.
Apex: Obtuse with an angle of approximately 110 degrees.
Tip: Very short, sharp, about 1/16" [1.6 mm.] in length.
Sides: Equal.
Surface: Irregularly furrowed near base.
External color of stone: Light yellowish brown [76. l.yBr].
Pit wall color when cracked: Pale orange yellow [73. p.OY].
Cavity surface color: Dark orange yellow [72. d.OY].
Average pit wall thickness: 1/8" [3.2 mm.].
Average length: 3/4" [19.1 mm.].
Average width: 5/8" [15.9 mm.].
Average breadth: 5/16" [7.9 mm.].
Tendency to split: None observed.

Kernel:

*Form.*—Oval.

*Skin color.*—Pale yellow [89. p.Y] when first removed.

*Pellicle color.*—Vivid yellow [82. v.Y].

*Vein color.*—Moderate yellow [87. m.Y].

*Taste.*—Bitter.

*Viable.*—Yes.

*Average length.*—½" [12.7 mm.].

*Average width.*—⅜" [9.5 mm.].

*Amygdalin.*—Moderate.

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: Not tested.

Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to its seed parent, 'Plumsweet VI' interspecific tree (U.S. Plant Pat. No. 18,687), by being self-unfruitful and by producing fruit that is a green and red two-tone in skin color, full red in flesh color, firm in texture, juicy, and sweet in flavor, but is distinguished therefrom by being easier to set, by producing fruit that is larger in size and that matures about five days earlier.

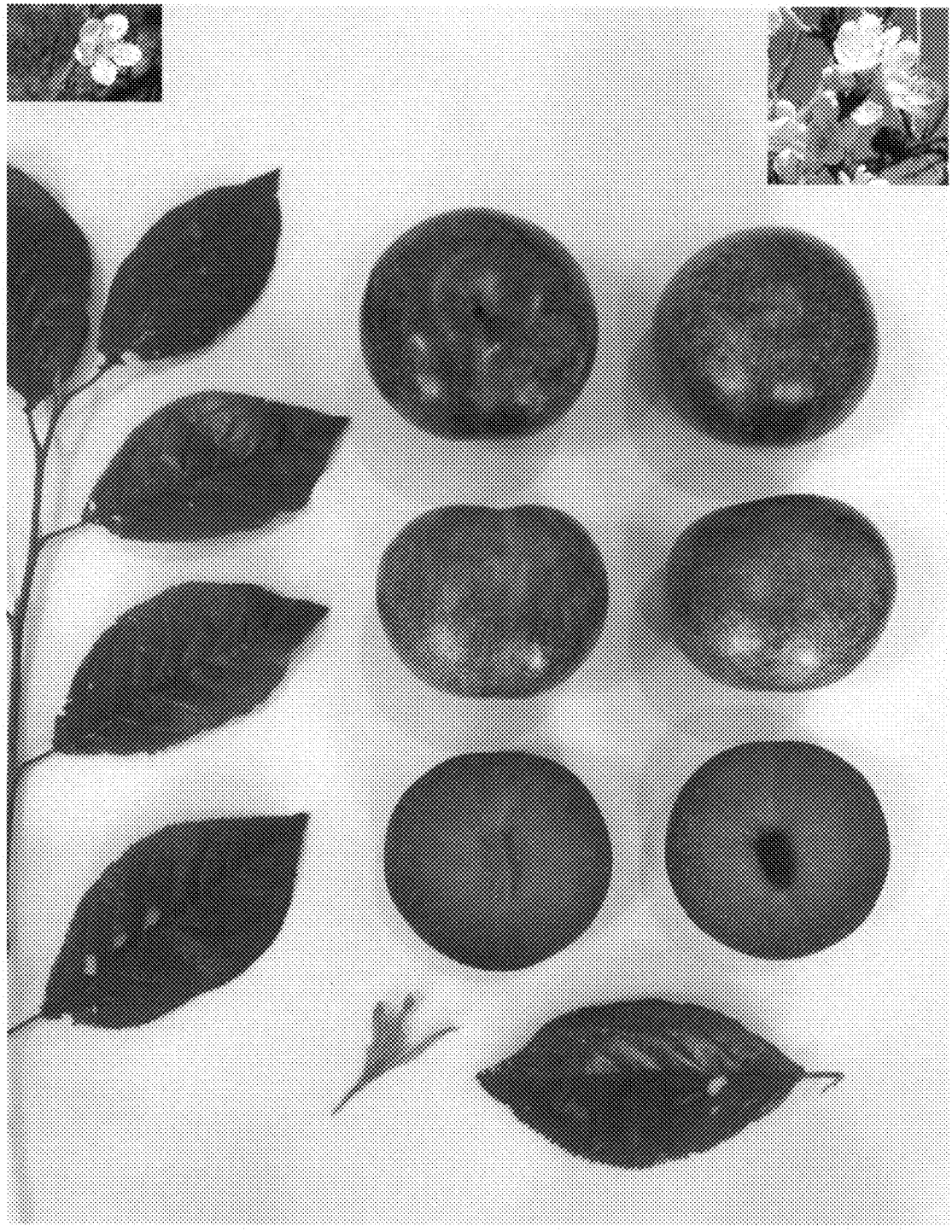

* * * * *